May 11, 1954 G. JACKMAN Plant Pat. 1,275
TAMARIX PLANT
Filed Dec. 15, 1952 2 Sheets-Sheet 1
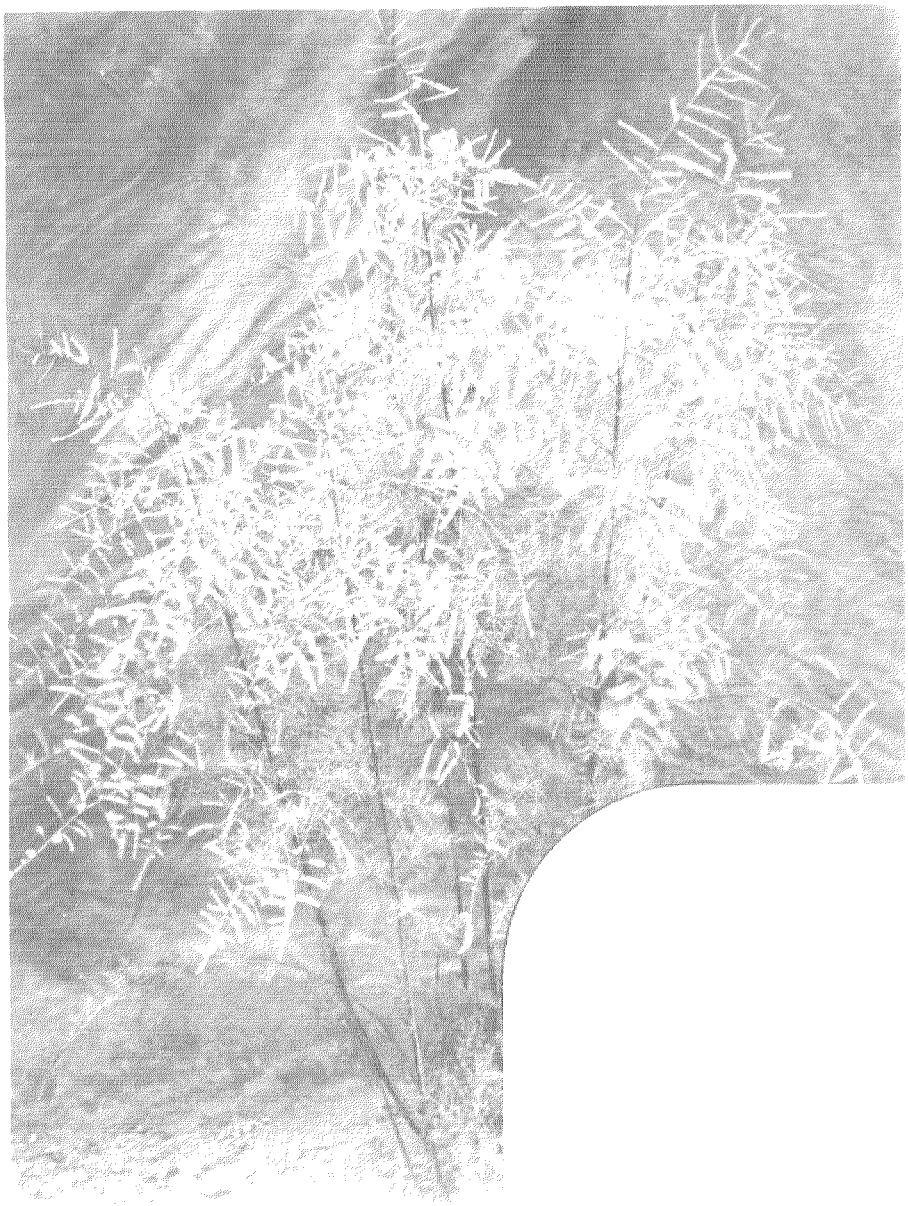
Inventor.
George Jackman
By: Robert Cobb
Attorneys May 11, 1954 G. JACKMAN Plant Pat. 1,275
TAMARIX PLANT
Filed Dec. 15, 1952 2 Sheets-Sheet 2
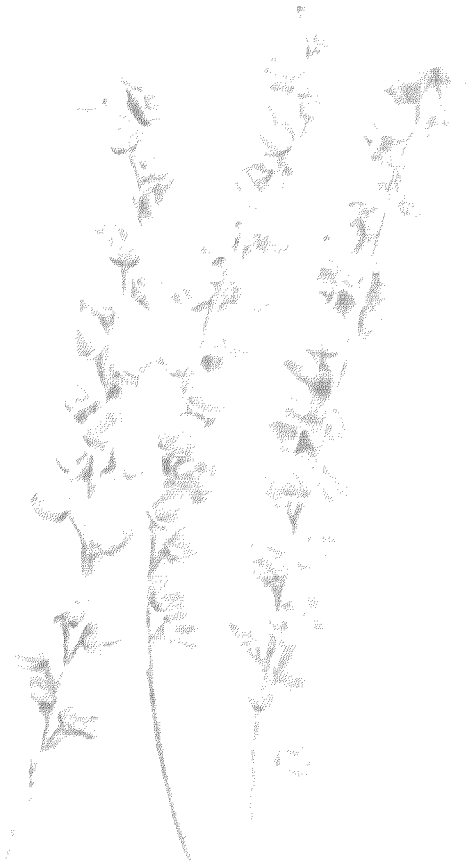
Inventor.
George Jackman
By: Robert Cobb
Attorneys.

Patented May 11, 1954 Plant Pat. 1,275

UNITED STATES PATENT OFFICE 1,275

TAMARIX PLANT

George Jackman, Woking, England, assignor to Gulf Stream Nursery, Inc., Red Bank, N. J., a corporation of New Jersey Application December 15, 1952, Serial No. 326,177

1 Claim. (Cl. 47—60)

The present invention relates to a new and distinct variety of Tamarix plant which originated as a sport of the variety *Tamarix Hispida Aestivalis* (unpatented). The new variety was discovered by me in my cultivated nursery at Woking, Surrey, England, where I was cultivating and growing the variety *Tamarix Hispida Aestivalis.* My attention was directed to the new sport by reason of the fact that I observed that one of the plants of *Tamarix Hispida Aestivalis* developed flowers and foliage of a color that was different from those of *Tamarix Hispida Aestivalis,* and on further development and test of the new sport, I found that it was otherwise definitely distinguished from *Tamarix Hispida Aestivalis,* as well as from all other Tamarix varieties of which I am aware.

In addition to the distinctions in color of the flowers and foliage of my new variety, it is characterized by its unusual habit of bearing small individual flowers which are gathered in large trusses and form drooping panicles at the top of each young shoot, instead of being substantially erect as in the parent variety *Tamarix Hispida Aestivalis.* This drooping characteristic of my new variety creates a most attractive effect in the nature of a cascade of Rose Madder color, which is the characteristic coloring of the flowers of my new variety. The new variety is prolific in its blooming habit, the blooms are very long-lasting, and the general decorative effect is enhanced by the very graceful, glaucous, lacy, bluish-green color of the foliage.

Asexual reproduction of my new variety by cuttings, both at Woking, Surrey, England, and at Wachapreague, Virginia, U. S. A., shows that the foregoing characteristics come true to form and are established and transmitted through succeeding propagations.

In the accompanying drawings, one sheet shows specimen plants of my new Tamarix variety in black-and-white, and another sheet shows details of typical specimen blooms on a greatly enlarged scale and in color.

The following is a detailed description of my new variety, with color terminology in accordance with the British color chart of the Royal Horticultural Society, except where general color terminology of ordinary dictionary significance is obvious:

Parentage: Sport of *Tamarix Hispida Aestivalis.*

*Plant*

(Observations made at Wachapreague, Virginia, U. S. A.)

Growth: Vigorous.

Form: Compact; growing to approximately six feet in height; terminated by large drooping trusses or panicles of flowers.

Foliage: Very graceful; glaucous; lacy.

*Leaves.*—Alternate; small and scale-like. Color—bluish-green. Shape—lanceolate to ovate.

Blooming habit: Prolific bloomer; blooms from July to September.

Flowers borne: Small, short-pedicelled individual flowers gathered in dense racemes from 1 to 2 inches long and forming large drooping panicles at top of each young shoot; panicles droop over and form a very decorative cascade-like effect.

Sepals: 5 in number.

Petals: 5 in number.

*Color.*—Rose Madder, Plate 23/3.

*Shape.*—Broadly elliptic-oblong.

Stamens: 5 in number.

Ovary: 1-celled, surrounded at the base by a more or less deeply lobed disk.

Seeds: Very minute.

Lasting quality of flowers: Long.

I claim:

A new and distinct variety of Tamarix plant, substantially as herein shown and described, characterized particularly as to novelty by its vigorous and compact habits of growth, by its prolific and very decorative cascade-like blooming habit resulting from small individual flowers gathered in large drooping panicles at the top of each young shoot, by the Rose Madder general color tonality of its flowers, and by its graceful, glaucous, lacy, bluish-green colored foliage.

No references cited.